US010086233B2

(12) United States Patent
Sechrest et al.

(10) Patent No.: US 10,086,233 B2
(45) Date of Patent: Oct. 2, 2018

(54) FITNESS EQUIPMENT WITH ANTHROPOMETRIC DATA ENHANCED WORKOUT GENERATOR

(71) Applicant: ATHLIOS, INC., Hermosa Beach, CA (US)

(72) Inventors: Michael Scott Sechrest, Hermosa Beach, CA (US); Mark R. Thompson, Chandler, AZ (US)

(73) Assignee: ATHLIOS, INC., Hermosa Beach, CA (US)

( * ) Notice: Subject to any disclaimer, the term of this patent is extended or adjusted under 35 U.S.C. 154(b) by 0 days.

(21) Appl. No.: 15/458,289

(22) Filed: Mar. 14, 2017

(65) Prior Publication Data

US 2017/0266497 A1  Sep. 21, 2017

Related U.S. Application Data

(60) Provisional application No. 62/308,426, filed on Mar. 15, 2016.

(51) Int. Cl.

| A63B 24/00 | (2006.01) |
| A63B 22/02 | (2006.01) |
| A63B 71/06 | (2006.01) |
| G16H 20/30 | (2018.01) |
| G06F 19/00 | (2018.01) |

(52) U.S. Cl.
CPC .......... *A63B 24/0075* (2013.01); *A63B 22/02* (2013.01); *A63B 24/0087* (2013.01); *A63B 71/0622* (2013.01); *G06F 19/00* (2013.01); *G16H 20/30* (2018.01); *A63B 2225/20* (2013.01); *A63B 2225/50* (2013.01); *A63B 2230/06* (2013.01); *A63B 2230/436* (2013.01)

(58) Field of Classification Search
CPC . A63B 24/00; A63B 24/0067; A63B 24/0082; A63B 24/0075; A63B 2230/06; A63B 2230/436; A63B 2225/50; A63B 2225/20; A63B 71/0622; A63B 22/02
See application file for complete search history.

(56) References Cited

U.S. PATENT DOCUMENTS

| 7,285,090 | B2 * | 10/2007 | Stivoric ................... A61B 5/01 600/300 |
| 7,905,817 | B2 | 3/2011 | Giannascoli et al. |
| 7,914,420 | B2 | 3/2011 | Daly et al. |
| 8,202,202 | B2 * | 6/2012 | McGlynn ............... A61B 5/486 482/9 |
| 8,864,630 | B2 | 10/2014 | Sperry |
| 8,950,256 | B2 | 2/2015 | Kautz et al. |

(Continued)

*Primary Examiner* — Glenn Richman
(74) *Attorney, Agent, or Firm* — Fulwider Patton LLP

(57) ABSTRACT

An exercise equipment and method for use is disclosed having a program that calls for user specific anthropometric data and then utilizes the data to create a user specific workout program based on the user's physical characteristics. The user inputs of personal anthropometric data includes, but is not limited to, sex, height, weight, goals, maximum heart rate, maximum run speed, maximum walk speed, and VO2 max. These inputs are used to optimize a workout program either in single use or multiple use applications. Moreover, data can be stored locally, on a network, or transferred to a cloud based repository for recall.

8 Claims, 3 Drawing Sheets

(56) References Cited

U.S. PATENT DOCUMENTS

| | | | |
|---|---|---|---|
| 2004/0220017 A1* | 11/2004 | Gordon | A63B 24/00 |
| | | | 482/8 |
| 2005/0239601 A1* | 10/2005 | Thomas | A63B 24/00 |
| | | | 482/1 |
| 2006/0189440 A1 | 8/2006 | Gravagne | |
| 2007/0219059 A1* | 9/2007 | Schwartz | A61B 5/0205 |
| | | | 482/8 |
| 2014/0278220 A1* | 9/2014 | Yuen | G01B 21/16 |
| | | | 702/150 |
| 2014/0378280 A1 | 12/2014 | Kristiansen et al. | |
| 2015/0104772 A1* | 4/2015 | Goel | G09B 5/02 |
| | | | 434/238 |
| 2015/0238819 A1 | 8/2015 | Volkerink et al. | |
| 2016/0051169 A1* | 2/2016 | Hong | A63B 71/06 |
| | | | 600/595 |
| 2016/0345829 A1* | 12/2016 | Kirby | G06F 19/3418 |
| 2017/0266498 A1* | 9/2017 | Sanders | A43B 3/0005 |

* cited by examiner

FITNESS EQUIPMENT WITH ANTHROPOMETRIC DATA ENHANCED WORKOUT GENERATOR

CROSS-REFERENCES TO RELATED APPLICATIONS

This application claims priority from U.S. Application No. 62/308,426, filed Mar. 15, 2016 incorporated by reference in its entirety.

BACKGROUND

Exercise has long been recognized for its many health benefits and, as a result, more and more people are turning to exercise as part of a daily regimen to improve fitness, lose weight, combat hypertension and improve one's mental health. Whether at the gym or at home, people are exercising more and enjoying the fruits of that labor. Gym memberships are on the rise, as is the purchase of home gym equipment that allow users to exercise in the privacy of one's home. Most gyms offer a wide array of stand alone fitness machines, from tread mills to stair climbers to rowing machines to weight lifting apparatus. In some cases, these machines offer some minor adjustments to the physical stature of the user, but the adjustments are typically incremental size modifications like the position of a pedals on an exercise bike or the seat position on a rowing machine. Unfortunately, these same machines many times come with a standard program that is one-size fits all, in that no adjustment or modification is made for the particular physiological characteristics of the user. As a result, a person with short legs may be asked to perform the same strides on a stair claimer as a long legged person, which can lead to inefficiencies, discomfort, and even injuries based on long term misapplication of the proper program. These issues can lead to a user quitting the equipment or even giving up an exercise program due to frustration over an improper or unsafe program that is ill-suited for the user.

SUMMARY OF THE INVENTION

The present invention relates to fitness equipment that includes a profile application to match user anthropometric characteristics of the user to the function of the machine. Many fitness machines include user queries about weight, but simply knowing how much someone weighs does not reveal much about their overall condition. The present invention utilizes various anthropometric measurements, i.e., systematic measurements of the size and shape of the human body, to formulate a workout program that is tailored to the specific user. For example, people of different heights have differing maximum walk and run speeds, and the present invention utilizes the user's size to design a cardio program for an exercise equipment, such as a treadmill, that accounts for the user's stride length and cardio condition. Utilizing profiles that change the function of the machine to optimize the user experience is safer and produces greater results than fitness equipment that do not take into account the user's anthropometrics.

These and other features of the present invention will best be understood by reference to the detailed description of the present invention along with the accompanying drawings.

DETAILED DESCRIPTION OF THE PREFERRED EMBODIMENTS

The present invention is an exercise equipment, and program for an exercise equipment, that inputs user specific anthropometric data and then utilizes the data to create a user specific workout program based on the user's physical characteristics. The user inputs of personal anthropometric data includes, but is not limited to, sex, height, weight, goals, maximum heart rate, maximum run speed, maximum walk speed, and $VO_2$ max. These inputs are used to optimize a workout program either in single use or multiple use applications. Moreover, data can be stored locally, on a network, or transferred to a cloud based repository for recall.

A goal of the present invention is to construct the industry's most personalized exercise experience. The present invention allows users to easily upload and download workouts and progressions, and the graphic user interface interacts with all leading applications and wearables. Further, there is tremendous flexibility in the configuration of the user interface for a broad base of users. Added features allow users to effect a machine reservation, EULAs and toggles that allow the facility to 'tune' the treadmill to their demographic. Moreover, the present invention has as a foundation an extremely robust web-based back end to allow machine auto-updates and integration with all third party asset and retention analytics groups. The present invention achieves each of these goals and more.

Figure 1:
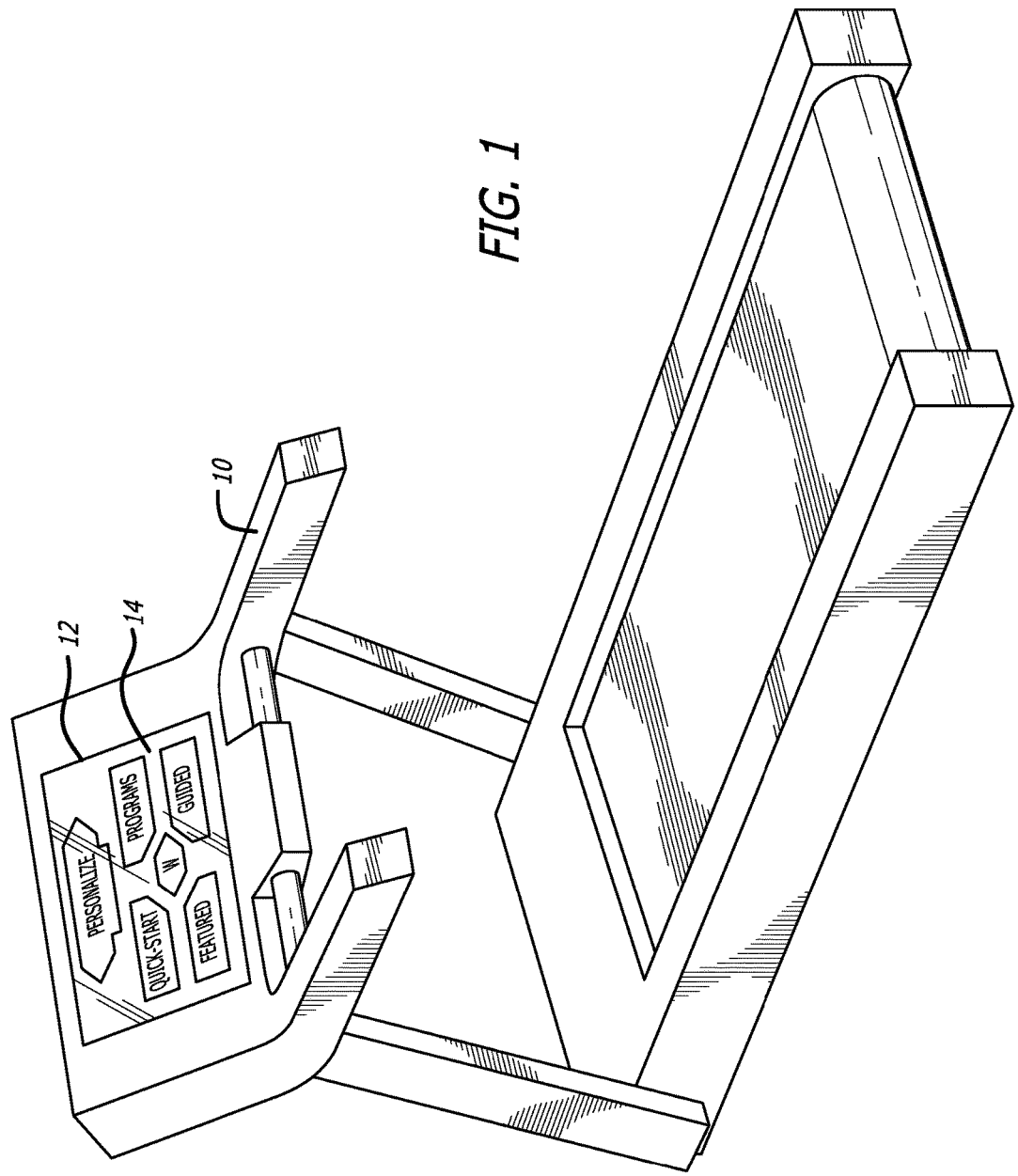
FIG. 1 is an exemplary view of a fitness apparatus embodying the present invention.

FIG. 1 illustrates an exemplary fitness apparatus 10 in the form of a treadmill that includes a display console 12 with a touchscreen user interface 14 for displaying a workout profile and for inputting user data. The fitness apparatus 10 can be any of the type of cardiovascular or resistive training machines for which a user can benefit from a custom workout profile, such as an exercise bicycle, a rowing machine, a stair climber, etc., and the type of fitness apparatus is not limiting to the present invention. The console 12 is a sturdy plastic or aluminum housing, for example, that supports a touchscreen or other display that can be viewed by the user while participating in the exercise program. The housing should be moisture resistant to avoid sweat and cleaning fluids from contaminating the housing's interior and the sensitive electronics protected therein. The display 14 will typically have a stand-by screen that includes options for a user to select, such as Quick-Start, Featured Programs, Programs, and Guided Programs. Each of these workout categories represent known examples of standard workouts that are designed for all users regardless of their anthropometric characteristics.

The display 14 of the present invention includes a "Personalize" option that allows the user to enter specific data about the user. The selection of the "Personalize" option will prompt the processor to request of the user certain data, such as the user's age, sex, height, weight, goals, maximum heart rate, maximum run speed (or other equipment maximum performance), maximum walk speed, and maximum volumetric oxygen intake. This personal anthropometric data may be stored by the fitness apparatus in a local storage, communicated to a local server via a Local Area Network (LAN) connection, or sent to a remote server via the internet or stored in the Cloud. The user can then recall such information on the next day when using this machine, or a commonly connected machine, so that the workout can be modified to match the user's goals and specific anthropometric characteristics. For example, a shorter runner will take fewer strides than a longer legged runner, so an equivalent running workout profile may call for a reduced strides per minute aspect of the workout. Alternatively, a person with a higher maximum run speed can tailor a workout that is designed to a specific fitness level based on the user's specific achieved fitness condition, rather than a profile without consideration of these user specific inputs.

Figure 2:
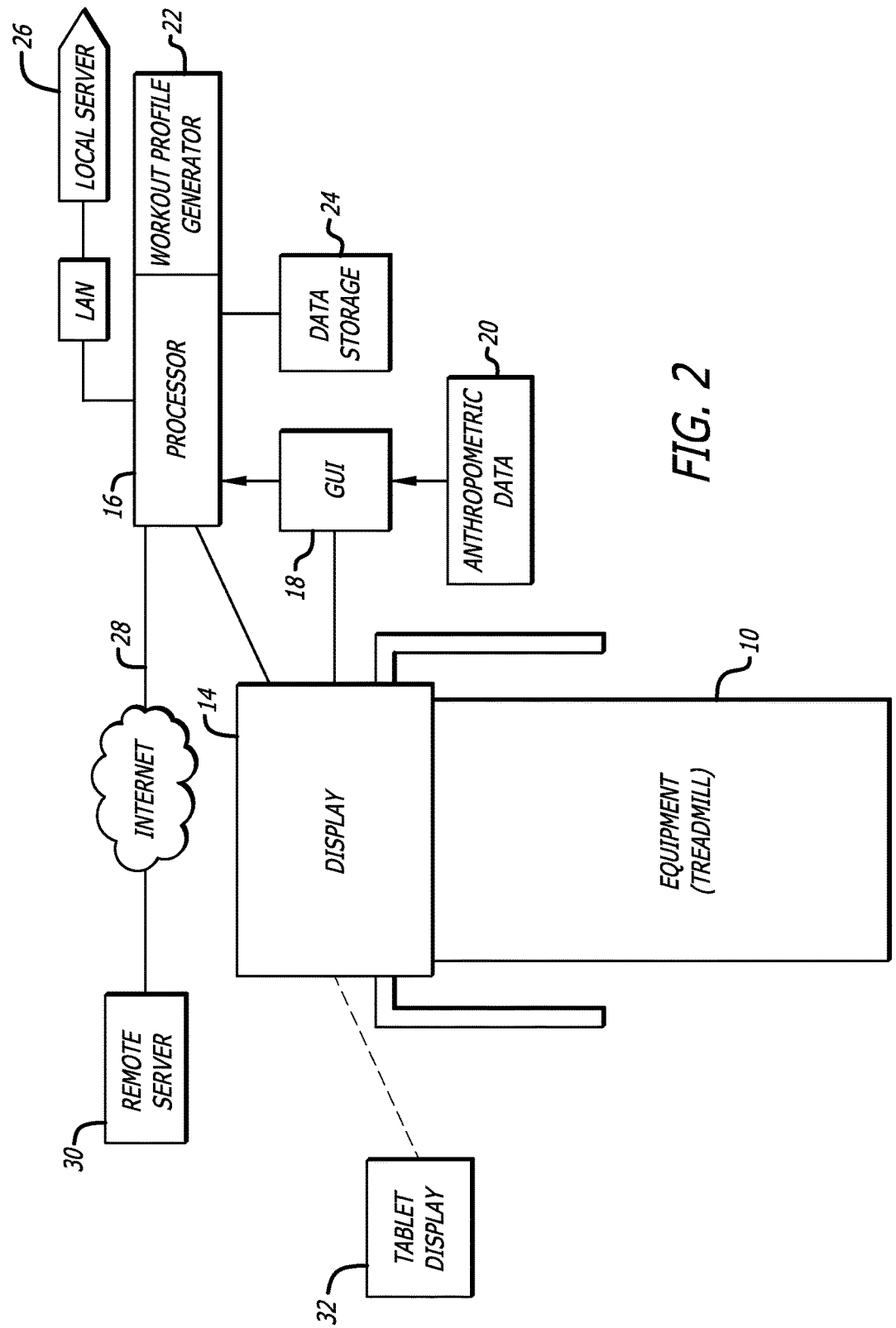
FIG. 2 is a schematic diagram of a first embodiment of the present invention.

FIG. 2 is a schematic of the fitness equipment and the relative components that make up the present invention. The actual workout equipment 10 includes a screen or display 14 that is connected to a processor 16 and a graphic user interface 18, preferably a touchscreen interface. User supplied anthropometric data 20 is supplied via the graphic user interface 18 to the processor 16, which includes a module running on the processor referred to as the workout profile generator 22. The workout profile generator 22 is a computer program that uses baseline workout profiles and then modifies the profiles based on the user supplied anthropometric data received from the graphic user interface 18 to generate a modified workout profile. The modified workout profile is then displayed on the display 14 and the exercise equipment operates based on this modified workout profile. The modified workout profile can be stored in a local data storage 24 for future use by the user, or sent via a LAN to a local server 26. Alternately, the workout profile can be sent via an internet connection 28 to a remote server 30 or a Cloud based storage solution for later recall by the user. In this way, the user can recall the user specified data and apply it to multiple machines and immediately begin a custom workout designed for the user's physical characteristics and fitness level.

Another feature of the present invention is the ability to mirror the display on a remote unit, such as a tablet 32, smartphone, or desktop computer, such that a trainer, coach, or physician can design or control the workout of the user. The ability to mirror the equipment's display 14, and the equipment's controls thereby, is a unique feature of the present invention.

Figure 3:
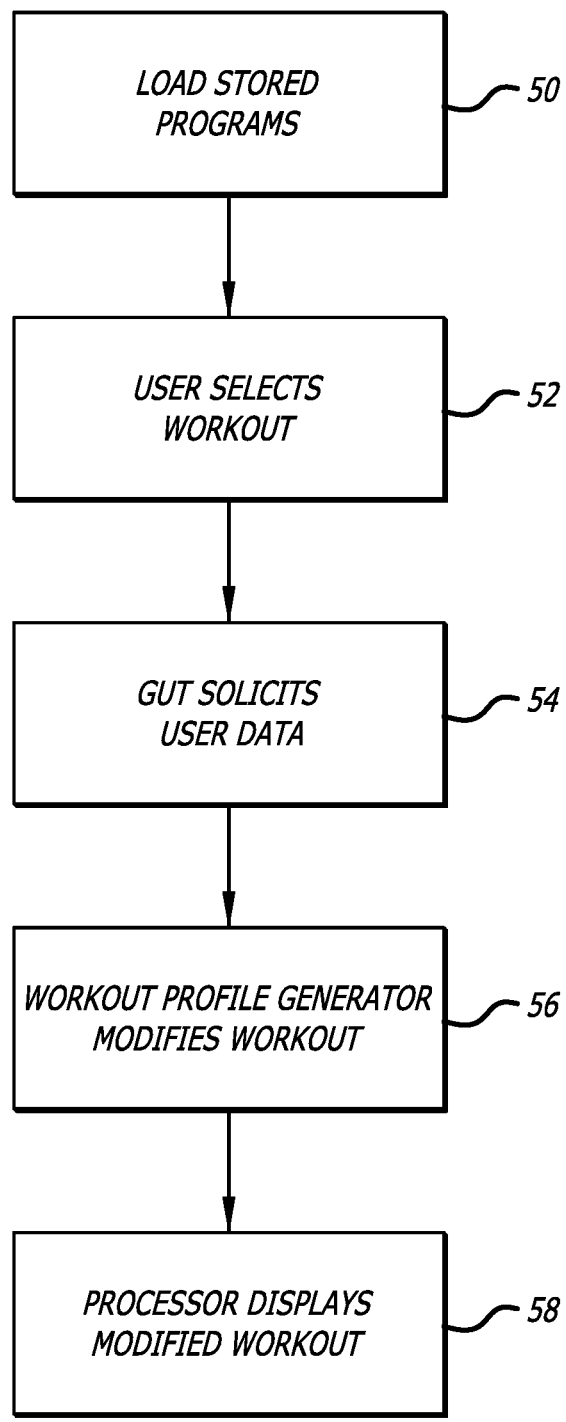
FIG. 3 is a flow chart of steps for carrying out a method of the present invention.

FIG. 3 illustrates a flow chart for a method of using the present invention. The user steps on the fitness equipment in step 50 and touches the touchscreen display 14, causing the stand-by mode to exit and the initial program screen to be displayed. The locally stored programs can be loaded onto into memory for use by the user, and in step 52 the user selects a workout for the present session. The GUI 18 then prompts the user to enter specific user supplied anthropometric data needed to customize the selected workout, such as height, maximum heart rate, and oxygen intake. In step 56, the processor causes the workout profile generator 22 to modify or customize the base workout profile selected into a new custom profile based on the user supplied anthropometric data. The new workout profile is then displayed on the display 14 in step 58 and the user begins his or her new modified workout.

The advantages of the present invention are that the user has a program that is specifically designed for his or her body type, fitness level, and specific personalized characteristics. This results in a more efficient and more targeted workout that is safer, and more likely to keep the user coming back to the selected equipment. The ability to download new base profiles from the internet and modify the profiles is an enhancement to the present invention, where the workout profile generator may be generally adapted to modify certain workout profiles based on known relationships between anthropometric information and workout performance.

The foregoing descriptions and depictions are not intended to be limiting, but rather illustrative only of the present invention. One of ordinary skill in the art would readily appreciate that many alterations and modifications could be made to the present invention, and the scope of the present invention is intended to include all such alterations and modifications. Accordingly, except where expressly stated to the contrary, the scope of the invention is understood to be guided by the appended claims using their plain and ordinary meanings, in light of but not limited by the foregoing discussion and drawings herein.

We claim:

1. A fitness apparatus system for exercise having a workout component, a first display, and a processor, the system comprising:
   a graphic user interface for inputting user specified size, shape, and characteristic of a human body data;
   a workout profile generator running on the processor, the workout profile generator adapted to receive the user specified data from the graphic user interface and generate an optimized user-specific workout profile using said user specified data to be displayed on the first display of a fitness apparatus;
   a remote data storage unit for storing the user's data;
   a data exchange for sending and receiving data from the remote data storage unit; and
   a second display remote from the first display, wherein the second display mirrors the first display.

2. The fitness apparatus of claim 1, further comprising a network where the user specified data is stored on a local server.

3. The fitness apparatus of claim 1, further comprising an internet connection where the user specified data is stored on a remote server.

4. The fitness apparatus of claim 1, wherein the user specified data includes a user's maximum apparatus capability.

5. The fitness apparatus of claim 1, wherein the specified data includes a user's maximum volumetric oxygen intake.

6. The fitness apparatus of claim 1, wherein the user specified data includes a user's maximum heart rate.

7. The fitness apparatus of claim 1, wherein the workout profile generator generates a multi-use profile.

8. The fitness apparatus of claim 1, wherein the workout profile generator adapts a user's physical size to a size specific workout profile.

* * * * *